(12) United States Patent
Cowe et al.

(10) Patent No.: US 11,944,788 B2
(45) Date of Patent: Apr. 2, 2024

(54) AUTO-INJECTOR

(71) Applicant: Owen Mumford Limited, Woodstock (GB)

(72) Inventors: Toby Cowe, Woodstock (GB); Matthew John Watts, Woodstock (GB); Dheeraj Ramakrishnan, Hungerford (GB); Richard Apsey, Hungerford (GB)

(73) Assignee: Owen Mumford Limited, Oxfordshire (GB)

( * ) Notice: Subject to any disclaimer, the term of this patent is extended or adjusted under 35 U.S.C. 154(b) by 544 days.

(21) Appl. No.: 16/761,552

(22) PCT Filed: Nov. 6, 2018

(86) PCT No.: PCT/EP2018/080364
§ 371 (c)(1),
(2) Date: May 5, 2020

(87) PCT Pub. No.: WO2019/086718
PCT Pub. Date: May 9, 2019

(65) Prior Publication Data
US 2020/0261652 A1 Aug. 20, 2020

(30) Foreign Application Priority Data
Nov. 6, 2017 (GB) .................................... 1718315

(51) Int. Cl.
A61M 5/20 (2006.01)
A61M 5/315 (2006.01)
A61M 5/46 (2006.01)

(52) U.S. Cl.
CPC ........ *A61M 5/2033* (2013.01); *A61M 5/3157* (2013.01); *A61M 5/46* (2013.01);
(Continued)

(58) Field of Classification Search
CPC .... A61M 5/2033; A61M 5/3157; A61M 5/46; A61M 2005/2013; A61M 2205/14;
(Continued)

(56) References Cited

U.S. PATENT DOCUMENTS

| | | | |
|---|---|---|---|
| 6,221,045 B1 | 4/2001 | Duchon et al. | |
| 2006/0079767 A1* | 4/2006 | Gibbs | A61M 5/14546 |
| | | | 600/432 |

(Continued)

FOREIGN PATENT DOCUMENTS

| | | |
|---|---|---|
| AU | 2015308670 A1 | 3/2017 |
| CA | 3006626 A1 | 7/2017 |

(Continued)

OTHER PUBLICATIONS

International Preliminary Report on Patentability (IPRP) from corresponding PCT Application No. PCT/EP2018/080364, dated May 12, 2020 (15 pages).

(Continued)

*Primary Examiner* — Theodore J Stigell
*Assistant Examiner* — Nidah Hussain
(74) *Attorney, Agent, or Firm* — Quarles & Brady LLP

(57) ABSTRACT

An auto-injector (100) for use with a primed safety syringe (200). The auto-injector comprises: a first detector (312) configured, after activation of the auto-injector, to detect movement of a plunger (206, 222) of the safety syringe to a point on a delivery stroke thereof that is indicative of full dose delivery of a substance from the safety syringe.

19 Claims, 5 Drawing Sheets

(52) U.S. Cl.
CPC . *A61M 2005/2013* (2013.01); *A61M 2205/14* (2013.01); *A61M 2205/3584* (2013.01); *A61M 2205/52* (2013.01); *A61M 2205/581* (2013.01); *A61M 2205/583* (2013.01); *A61M 2205/587* (2013.01)

(58) Field of Classification Search
CPC ...... A61M 2205/3584; A61M 2205/52; A61M 2205/581; A61M 2205/583; A61M 2205/587
USPC .......................................................... 604/218
See application file for complete search history.

(56) References Cited

U.S. PATENT DOCUMENTS

| | | | |
|---|---|---|---|
| 2010/0262434 A1* | 10/2010 | Shaya | A61B 5/7475 705/3 |
| 2013/0274671 A1 | 10/2013 | Jennings et al. | |
| 2013/0281929 A1 | 10/2013 | Jennings et al. | |
| 2014/0012229 A1* | 1/2014 | Bokelman | A61M 5/2033 604/154 |
| 2014/0312074 A1 | 10/2014 | Madsen et al. | |
| 2014/0378943 A1* | 12/2014 | Geipel | A61M 5/16809 604/152 |
| 2016/0022915 A1 | 1/2016 | Cowe | |
| 2016/0193415 A1 | 7/2016 | Cowe | |
| 2016/0243310 A1 | 8/2016 | Dasbach | |
| 2017/0281877 A1 | 10/2017 | Marlin et al. | |
| 2018/0296761 A1* | 10/2018 | Cowe | A61M 5/326 |
| 2018/0369488 A1* | 12/2018 | Carlsson | A61M 5/3157 |

FOREIGN PATENT DOCUMENTS

| | | |
|---|---|---|
| GB | 2534599 A | 8/2016 |
| JP | 2014516634 A | 7/2017 |
| WO | 2010035056 A1 | 4/2010 |
| WO | 2017050781 A1 | 3/2017 |
| WO | 2017114910 A1 | 7/2017 |
| WO | 2017125733 A1 | 7/2017 |
| WO | 2017174668 A1 | 10/2017 |

OTHER PUBLICATIONS

International Search Report and Written Opinion of the International Searching Authority from corresponding PCT Application No. PCT/EP2018/080364, dated Mar. 28, 2019 (22 pages).
Search Report, related UK Application No. GB 1718315.3, dated Apr. 26, 2018, 9 pages.
Office Action from corresponding Japanese Application No. 2020-524755, dated Jun. 7, 2022 (7 pages).

* cited by examiner

AUTO-INJECTOR

CROSS-REFERENCE TO RELATED APPLICATIONS

This application represents the U.S. National Stage of International Application No. PCT/EP2018/080364 filed Nov. 6, 2018, which claims priority to British Patent Application Serial No. GB 1718315.3, filed Nov. 6, 2017, and entitled, "AUTO-INJECTOR", all of which are incorporated herein by reference in their entirety.

TECHNICAL FIELD

The invention relates to auto-injectors for use with syringes. The invention may relate to, but need not be limited to, safety auto-injectors and/or auto-injectors for use with safety syringes.

BACKGROUND

Safety syringes typically include some form of safety mechanism to protect healthcare workers from a hypodermic needle of the syringe after it has been injected into a patient. Exemplary safety syringes may include a shroud or sheath for covering the needle after use of the syringe. Other exemplary syringes may cause the needle to retract within the barrel of the syringe.

Safety syringes may be broadly split into 'active' and 'passive' safety syringes. Active safety syringes typically require some action by a user of the syringe to engage the safety mechanism. Such action may be taken after removal of the needle from the patient, or may be taken during removal of the needle from the patient. Passive safety syringes typically engage the safety mechanism without any specific action by the user, that is, without any action other than that usually taken to use the syringe.

An auto-injector is a device for receiving a syringe and for driving a syringe plunger of the syringe into a barrel of the syringe, typically without any driving force being applied by the user, although some force may be required for activation. Typically, an auto-injector includes a plunger driver, such as a spring, that is arranged to provide a force to drive the syringe plunger into the barrel. The plunger driver is typically activated by operation of a button or other release mechanism on the auto-injector. A safety auto-injector may be one which includes a shroud that may be deployed to a position covering a needle of a syringe received within the auto-injector after use of the auto-injector. The shroud of the auto-injector may be deployed under a force applied by a shroud driver.

SUMMARY

According to the invention in an aspect, there is provided an auto-injector for use with a safety syringe, which may be a primed safety syringe, the auto-injector comprising: a first detector configured, after activation of the auto-injector, to detect movement of a plunger of the safety syringe to a point on a delivery stroke thereof that is indicative of full dose delivery of a substance from the safety syringe.

Optionally, the auto-injector further comprises a second detector for detecting that the device is in a closed state, which may comprise engagement between a barrel portion and a plunger portion.

Optionally, the first detector is configured to be operable in dependence on the second detector having detected such engagement.

Optionally, the auto-injector further comprises a third detector configured to detect the presence of the safety syringe.

Optionally, the first detector is configured to be operable in dependence on the third detector having detected the presence of the safety syringe.

According to the invention in a first aspect, there is provided an auto-injector for use with a safety syringe, the auto-injector comprising: a main body that is openable for receiving the safety syringe and closable before operation of the auto-injector; a first detector configured, after activation of the auto-injector, to detect movement of a plunger of the safety syringe to a point on a delivery stroke thereof that is indicative of full dose delivery of a substance from the safety syringe; a second detector configured to detect that the housing is in a closed position; and a third detector configured to detect a presence of the safety syringe, wherein the first detector is configured to be operable in dependence of at least one of the second detector having detected engagement between the barrel portion and the plunger portion and the third detector having detected the presence of the safety syringe.

Optionally, the main body comprises a hinged door openable for receiving the safety syringe and closable before operation of the auto-injector.

Optionally, the main body comprises: a barrel portion configured to receive a barrel of the safety syringe; and a plunger portion configured to receive a plunger of the safety syringe, wherein the barrel portion and the plunger portion are configured for detachable engagement, and wherein the main body is in the open position when the plunger portion and the barrel portion are detached.

Optionally, the first detector comprises a switch, and optionally a micro-switch, operable by a part of the safety syringe during the delivery stroke of the plunger of the safety syringe.

Optionally, the switch is operable by the syringe plunger at the point on the delivery stroke.

Optionally, the point on the delivery stroke is reached before completion of the delivery stroke.

Optionally, a distance between the point on the delivery stroke and the point of completion of the delivery stroke is sufficient to account for manufacturing tolerances in the safety syringe.

Optionally, the auto-injector further comprises one or more indicators configured based on data received from the first detector to indicate whether the full dose was delivered.

Optionally, the auto-injector further comprises a processor configured to receive signals from the first detector and to control a transmitter to transmit dose data to a user device, the transmitted data indicating whether the full dose was delivered.

Optionally, the processor is further configured to time-stamp the dose data, the auto-injector further comprising a memory for storing the dose data, optionally until a connection to the user device is established by the transmitter.

Optionally, the second detector comprises a switch and optionally a micro-switch.

Optionally, the switch is operable by a feature of the barrel portion during engagement with the plunger portion, or wherein the switch is operable by a feature of the plunger portion during engagement with the barrel portion.

Optionally, the second detector is positioned in the plunger portion.

Optionally, the auto-injector further comprises a receiver configured to receive a signal emitted from a device of the safety syringe and comprising syringe data identifying one or more parameters related to the safety syringe.

Optionally, the receiver forms part of a Radio Frequency Identification, RFID, device configured to transmit a Radio Frequency, RF, signal to cause the device of the safety syringe to emit the received signal.

Optionally, the processor is configured to include the syringe data in the dose data for transmission by the transmitter.

According to the invention in another aspect, there is provided an auto-injector for use with a safety syringe, the auto-injector comprising: a receiver configured to receive a signal emitted from a device of the safety syringe and comprising data identifying one or more parameters related to the safety syringe.

Optionally, the auto-injector further comprises a main body that is openable for receiving the safety syringe and closable before operation of the auto-injector.

Optionally, the main body comprises: a barrel portion configured to receive a barrel of the safety syringe; a plunger portion configured to receive a plunger of the safety syringe, wherein the barrel portion and the plunger portion are configured for detachable engagement.

Optionally, the receiver forms part of a Radio Frequency Identification, RFID, device configured to cause the device of the safety syringe to emit the received signal.

Optionally, the one or more parameters related to the safety syringe comprise one or more of: the batch of a substance within the barrel of the syringe; the date that the barrel was filled with the substance; and an identification of the substance.

Optionally, the auto-injector further comprises a plunger driver for coupling to a plunger head of the syringe when the syringe is fitted within the auto-injector, and configured to drive a plunger into a barrel of the syringe, wherein the plunger driver is positioned on the auto-injector such that it is below the plunger head when the syringe is and fitted within the auto-injector.

Optionally, the plunger driver is positioned such that it is below the plunger head after use of the syringe.

Optionally, the plunger driver is configured to couple to at least one arm coupled to the plunger head and extending towards a needle end of the auto-injector when the syringe is fitted thereto.

Optionally, the plunger driver comprises at least one compression spring. Optionally, the spring forms a channel within the barrel portion configured to receive the syringe therein.

Optionally, the auto-injector further comprises a safety syringe.

Optionally, the syringe comprises: a plunger having a head; and at least one arm extending longitudinally from the head of the plunger towards a needle end of the safety syringe and configured to engage with the plunger driver, such that extension of the plunger driver drives the plunger into a barrel of the syringe.

According to the invention in a further aspect, there is provided a syringe for use within an auto-injector, the syringe comprising a device configured to emit a signal comprising data identifying one or more parameters related to the syringe.

Optionally, the device comprises an RFID tag.

Optionally, the one or more parameters related to the syringe comprise one or more of: the batch of a substance within the barrel of the syringe; the date that the barrel was filled with the substance; and an identification of the substance.

BRIEF DESCRIPTION OF THE DRAWINGS

Exemplary embodiments of the invention are disclosed herein with reference to the accompanying drawings, in which.

DETAILED DESCRIPTION

Generally, disclosed herein are auto-injectors for use with a syringe and/or a safety syringe. Exemplary auto-injectors may comprise a first detector, which may be a delivery detector, configured to detect whether a plunger of a syringe within the auto-injector has reached a point on the delivery stroke that is indicative of full delivery of a substance, such as a drug, from within a barrel of the syringe. Other exemplary auto-injectors may comprise a receiver, which may be a Radio Frequency Identification (RFID) reader that forms part of an RFID system. The syringe may include an RFID tag that may emit a signal comprising data about the syringe and/or a substance contained in the barrel of the syringe.

In exemplary auto-injectors, a plunger driver (e.g. a compression spring) may be configured to apply a force to a plunger to drive it into a barrel of the syringe. The plunger driver may be located below a head of the plunger of a pre-filled syringe, which may be termed a primed syringe, received within the auto-injector. A syringe is considered to be primed when it contains a drug (or other substance) and has not been used, that is, when the plunger is drawn out of the barrel and there is a substance in the barrel for injection into a subject. Further, the term "below" the head of the plunger may encompass arrangements where the plunger driver is entirely below the head of the plunger. The plunger driver may be adjacent to or surrounding the barrel of the syringe. Because the plunger driver is not located above the plunger head, exemplary arrangements allow for the inclusion of other features in the space created, such as detectors, a processor, a transmitter and/or a receiver or RFID reader, which are discussed herein.

Exemplary plunger drivers may be fixed to the auto-injector at one end and configured to connect at an opposed end to one or more arms extending longitudinally from the head of the plunger towards a needle end of the syringe. Extension of the plunger driver towards the needle end applies a force to the one or more arms, thereby driving the plunger down into the barrel of the syringe. The syringe may be a safety syringe comprising a sheath connected to a head of a safety plunger by the arms, as described below. In such arrangements, a needle end of the plunger driver (e.g. a spring) may connect either to the arms or the sheath. In an exemplary arrangement, the plunger driver is located beneath an opening of the barrel of the syringe when fitted within the auto-injector. In a specific exemplary arrangement, the plunger driver is located beneath a flange at an opening of the barrel of the syringe when fitted within the auto-injector.

Figure 1:
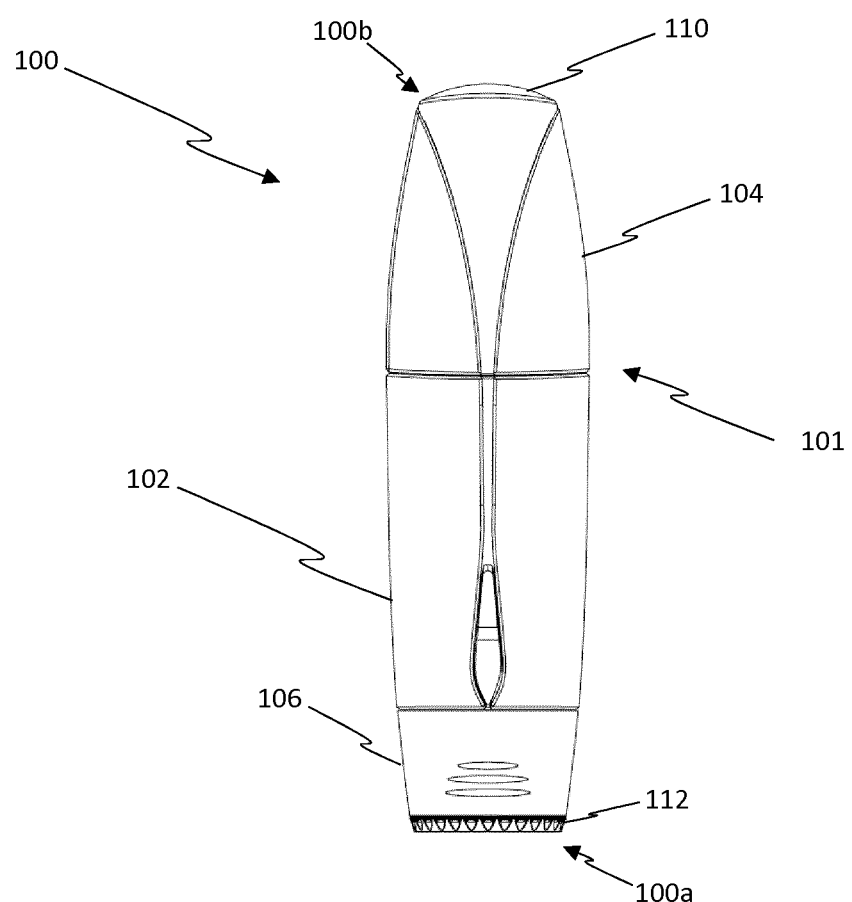
FIG. 1 is an isometric view of an auto-injector.

FIG. 1 shows an exemplary auto-injector 100. The auto-injector 100 comprises a main body 101. The main body 101 is configured to be openable for receipt of a syringe therein and closeable for operation of the auto-injector.

As will be appreciated by the skilled person, there are a number of ways in which an openable main body may be formed. In the specific embodiment shown in FIG. 1, the main body 101 comprises a barrel portion 102 and a plunger portion 104. The barrel portion 102 is configured to receive a barrel of a syringe. That is, the barrel of the syringe is at least partly contained within the barrel portion 102 when the syringe is fitted within the auto-injector 100. The plunger portion 104 is configured to receive a plunger of the syringe when it is fitted within the auto-injector. That is, the plunger of the syringe is at least partly contained within the plunger portion 104 when the syringe is fitted within the auto-injector 100. The barrel portion 102 and the plunger portion 104 may be configured for detachable engagement. The auto-injector may be opened by disengaging the plunger portion 104 from the barrel portion 102 and closed by re-engaging the plunger portion 104 and the barrel portion 102.

In other arrangements, the main body 101 may comprise a hinged door. The hinged door may be moveable between an open position and a closed position. The hinged door may be positioned on a front face of the main body 101. The hinged connection of the hinged door to the remainder of the main body 101 may be positioned at a rearward or plunger end of the main body.

When the hinged door is in the open position, the syringe may be received within the main body 101. Specifically, when the hinged door is in the open position, a recess within the main body 101 may be exposed. The recess may be configured to receive and optionally retain the safety syringe ready for operation by the auto-injector.

The hinged door is moveable into a closed position for operation of the auto-injector. That is, when the hinged door is closed and a safety syringe is received within the main body 101, the auto-injector may be in a state ready for operation.

In other arrangements, a door may be slidable or removable so as to expose the recess in the main body 101 and allow the safety syringe to be received therein. This and other arrangements will be readily understood by the skilled person.

The specific description below is provided in respect of the exemplary auto-injector 100 shown in the drawings. However, as will be readily understood, the relevant features of that auto-injector may be included in other exemplary auto-injectors, such as those mentioned above.

Generally, exemplary auto-injectors (and syringes) disclosed herein can be defined as having a needle end 100a and a plunger end 100b. These features will be used herein to aid description of the auto-injectors disclosed.

The auto-injector 100 further comprises a rigid needle shield (RNS) remover 106. The RNS remover 106 is configured for slidable extension away from the barrel portion 102 from a first position, in which the RNS is fitted to the syringe, to a second position, in which the RNS is pulled away from a needle of the syringe. In other arrangements, the RNS remover 106 may be rotated to move it from a first position to a second position. The rotation may result in extension of the RNS remover 106 away from the barrel portion 102. The RNS remover 106 may couple to an RNS of a syringe fitted within the auto-injector 100 such that extension of the RNS remover 106 removes the RNS. An aperture (not shown in FIG. 1) in the RNS remover 106 allows the RNS of the syringe to fall from the auto-injector 100 after removal.

The barrel portion 102 comprises a housing configured to surround a syringe barrel received therein. The barrel portion 102 has a main body that is broadly elliptical in cross section. The main body extends away from the needle end 100a towards an opening at the plunger end 100b that is configured to receive the barrel of the syringe. The opening may be large enough to accommodate a finger flange at an opening of the barrel of the syringe or a handle portion that is fitted to the barrel. The handle portion may be configured to receive index and middle fingers of a user when the syringe is used outside of the auto-injector 100. The opening of the barrel portion 102 is configured for removable connection to the plunger portion 104.

The plunger portion 104 comprises a housing configured to surround the plunger of the syringe when fitted within the auto-injector 100. The plunger portion 104 comprises a main body that is broadly elliptical in cross section. The main body of the plunger portion 104 extends away from a plunger end 100a towards an opening at the needle end 100a that accommodates the finger flange or a handle portion that is fitted to the barrel. The opening of the plunger portion 104 is configured for removable connection to the barrel portion 102. The plunger portion 104 may further comprise a button 110 or other activation device for activating the auto-injector 100 when a syringe is fitted therein.

The RNS remover 106 is broadly elliptical or circular in cross section. The RNS remover 106 may comprise a lip 112 around a needle end thereof to provide greater grip for a user wishing to extend the RNS remover 106.

Figure 2A:
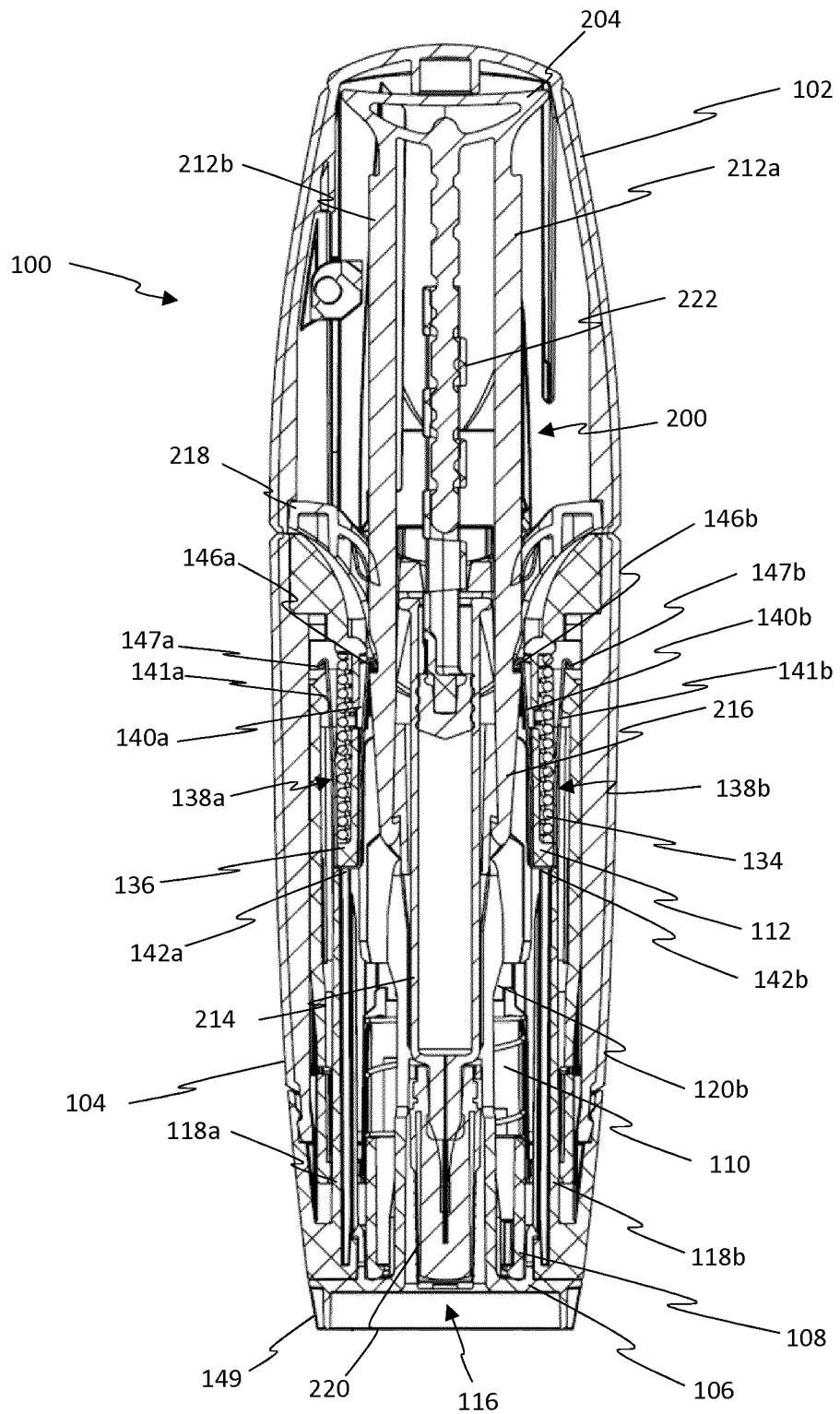
FIG. 2*a* is a cross section through an auto-injector.
Figure 2B:
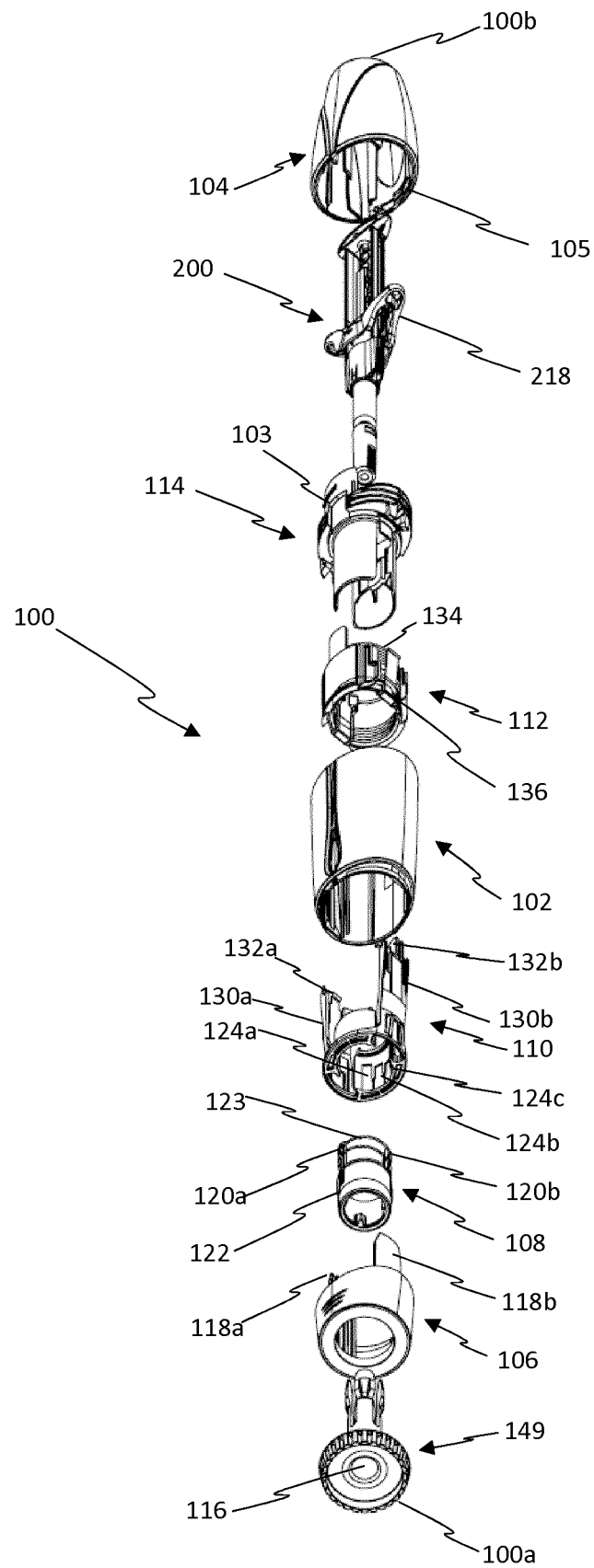
FIG. 2*b* is an exploded view of an auto-injector.

FIG. 2a shows a section through an exemplary auto-injector 100 and FIG. 2b shows an exploded view of an exemplary auto-injector 100. The auto-injector 100 comprises a barrel portion 102, a plunger portion 104 and a RNS remover 106. The barrel portion 102 houses a depth adjustor 108, a contact actuator 110, a carrier 112 and a body 114. A safety syringe 200 is also shown in FIG. 1a and this may be fitted within the auto-injector 100.

The barrel portion 102 is configured for removable connection with the plunger portion 104.

The plunger portion 104 may be configured for connection to the barrel portion 102 under a linear force applied by a user, and disconnected from the barrel portion 102 under a rotational force. The exemplary auto-injector 100 comprises discrete threaded sections on both the barrel portion 102 and the plunger portion 104. The body 114 comprises a barrel thread 103. The body 114 is configured to be fitted within an opening at a plunger end of the barrel portion 102 and comprises at least one guide configured to enter the plunger portion 104 when fitted to the barrel portion 102. The barrel thread is formed on the guide. The plunger portion 104 comprises a corresponding plunger thread 105 positioned at an opening at a needle end thereof.

In the exemplary auto-injector 100, the barrel thread 103 and the plunger thread 105 do not extend 360 degrees around the barrel portion 102 and the plunger portion 104. Rather, the barrel portion 102 and the plunger portion 104 comprise a plurality of discrete threaded sections that are angularly separated from each other about an opening of the barrel portion 102 and the plunger portion 104. In the auto-injector 100, the barrel portion 102 and the plunger portion 104 comprise two threads formed at opposed sides of the openings of the barrel portion 102 and the plunger portion 104, respectively.

In the exemplary auto-injector 100, the linear force applied by the user to connect the barrel portion 102 and the plunger portion 104 may bring the barrel thread 103 and the plunger thread 105 into engagement. This may be by a snap fit or clip fit arrangement which causes the threaded sections to ride over one another under the applied force. Once the barrel thread 103 and the plunger thread 105 are engaged, the plunger portion 104 may be disconnected from the barrel portion 102 by the relative rotation of the barrel portion 102 and the plunger portion 104, which moves the discrete barrel thread 103 out of alignment with the discrete plunger thread 105.

The barrel portion 102 and the plunger portion 104 may be disconnected to allow the insertion of a syringe 200 into the auto-injector 100 and reconnected once the syringe 200 has been inserted. Further, when a syringe 200 is fitted within the auto-injector 100, rotation of the plunger portion 104 with respect to the barrel portion 102 rotates the syringe 200 such that a part of the syringe 200 rides over a cam surface to translate the rotational movement of the syringe to linear movement, which acts to decouple the syringe from the barrel portion 102. Alternatively, rotation of the syringe 200 by rotation of the plunger portion 104 deforms the coupling members retaining the syringe 200 within the barrel portion 102 such that the syringe is decoupled from the barrel portion 102.

In exemplary arrangements, the barrel portion 102 (or the body 114 within the barrel portion 102) may be shaped to interact with a handle portion 218 of a safety syringe 200 such that a cam surface 115 is formed. The cam surface 115 is configured to translate rotational movement of the safety syringe 200 into linear movement of the safety syringe 200. In the example shown, the substantially oval opening in the body 114 interacts with the underside of the handle portion 218 of the syringe 200, which forms a ramped surface, to produce the linear movement. This linear movement may release the syringe 200 from captive coupling with the barrel portion 102, which may extract the syringe 200 from the barrel portion 102.

The RNS remover 106 is configured for removable connection with the barrel portion 102. The RNS remover 106 may be fully removed (i.e. separable) from the barrel portion 102. The RNS remover 106 may be configured for reattachment to the barrel portion 102 after use of the auto-injector 100 by application of force by a user to insert features of the RNS remover 106 into the barrel portion 102, as explained below.

The RNS remover 106 further comprises prongs 118a, 118b. The prongs 118a-b are configured to be received within the barrel portion 102 when the RNS remover 106 is connected to the barrel portion 102. The prongs 118a, 118b comprise a spring compression surface that is configured to couple to the compression spring 134 when the RNS remover 106 is reconnected to the auto-injector 100 for priming the compression spring 134.

The RNS remover 106 may connect to an RNS of a syringe 200 fitted within the auto-injector 100 such that removal of the RNS remover 106 from the barrel portion 102 removes the RNS. An aperture 116 in the RNS remover 106 allows the RNS of the syringe 200 to fall from the auto-injector 100 after removal of the RNS remover 106. The RNS remover 106 may also comprise a dial component 149 configured to rotate the depth adjustor 108 and operation of which is explained below.

The depth adjustor 108 is configured to partially protrude from the barrel portion 102 of the auto-injector 100 before use thereof. The depth adjustor 108 may be brought into contact with the skin of a user once the RNS remover 106 has been removed. The depth adjustor 108 is configured to be slidably and/or rotatably received within the barrel portion 102 of the auto-injector 100. Slidable movement of the depth adjustor 108 into the barrel portion 102 exposes the needle of the syringe 200 from a needle end of the depth adjustor 108 and therefore allows insertion of the needle into the skin of a patient. In the exemplary auto-injector 100, the depth adjustor is slidably and rotatably received within the contact actuator 110.

The depth adjustor 108 comprises lips 120a-b and a protrusion 122. The lips 120a-b are configured to engage with a surface of the contact actuator 110 to limit extension of the depth adjustor 108 and therefore its protrusion from the barrel portion 102. The depth adjustor may be biased towards a needle end 100a of the auto-injector 100 by a compression spring 123. The protrusions 122 are configured to engage with a mechanical end stop to limit insertion of the depth adjustor into the barrel portion and therefore limit insertion of the needle into the patient.

The contact actuator 110 comprises an aperture within which the depth adjustor 108 is received. The depth adjustor 108 may be of a smaller diameter than the diameter of the aperture such that the depth adjustor 108 may be telescopically received by the contact actuator 110. This arrangement allows axial and rotational movement of the depth adjustor 108 with respect to the contact actuator 110.

It is noted that exemplary auto-injectors are configured for use with the safety syringe 200. The exemplary syringe 200 shown in FIGS. 2a and 2b is fitted within the auto-injector 100 and is a safety syringe. A plunger 206 is a safety plunger coupled to a sheath 216 and comprises a plunger head 204 and two arms 212a, 212b extending from opposed sides of the plunger head 204. The arms 212a, 212b connect the plunger head 206 to the sheath 216. The arms 212a, 212b are slidable along the outside of the barrel 214 such that the sheath 216 moves along the outside of the barrel 214 on application of a force to the plunger head 204.

A handle portion 218 comprises a main body and flanges extending laterally from the main body. The main body comprises a portion that surrounds the barrel and is fixed thereto. The flanges form a finger grip and, when the safety syringe is used outside of the auto-injector 100, are configured to receive the index finger and middle finger of a user while the thumb applies a force to the plunger head 204 of the safety plunger. The sheath 216 may be partially received within the main body of the handle portion 218 when the safety plunger 206 is at the outermost part of its stroke. At least a portion of the sheath 216 protrudes from the main body of the handle portion 218.

The arms 212a, 212b of the safety plunger 200 pass through the handle portion 218 such that the safety plunger 206 may move along its stroke relative to the handle portion 218 and, therefore, the barrel 214. The sheath 216 is configured to travel along the outside of the barrel 214 with the inward stroke of the safety plunger 206 until the sheath 216 at least partially covers a needle of the safety syringe 200. At the innermost point of the stroke of the safety plunger 206, the end of the sheath 216 is beyond the end of the needle, such that the sharp point of the needle is not exposed.

The safety plunger 206 is coupled to a syringe plunger 222 during a first part of its inward stroke and so the syringe plunger 222 is driven into the barrel 214 on movement of the safety plunger 206 along its inward stroke. The safety plunger 206 decouples from the syringe plunger 222 at a point on the inward stroke, which may be when the syringe plunger 222 has expelled all of a medicament or drug from the barrel 214. After decoupling, the safety plunger 206 may move longitudinally relative to the syringe plunger 222 and continued movement of the safety plunger 206 moves the sheath 214 into a position covering the needle. In this sense, decoupling may refer to longitudinal decoupling. There may exist a rotational coupling of the safety plunger 206 and the syringe plunger 222 after longitudinal decoupling.

Decoupling of the safety plunger 206 and the syringe plunger 222 may be by means of relative rotation between the safety plunger 206 and the syringe plunger 222 to disengage one from the other. For example, a decoupling mechanism may comprise a lug on the syringe plunger 222 configured to move between engagement and disengagement with a coupling recess in the safety plunger 206. The movement between engagement and disengagement may be by rotation of the syringe plunger 222 relative to the safety plunger 206.

In some arrangements, the safety syringe 200 may comprise a rate controlling means for controlling a rate of travel of the safety plunger 206 after decoupling. The rate controlling means may comprise a rate limiting member coupled to the safety plunger 206 and configured to engage with the syringe plunger 222. The rate limiting member may comprise a first screw thread 224 and the syringe plunger 222 may comprise a second screw thread that is configured to engage with the first screw thread 224 to rotate the syringe plunger 222 on linear movement of the safety plunger 206 after decoupling.

In such arrangements, the decoupling mechanism may comprise a rotation prevention member configured to prevent rotation of the syringe plunger 222 before decoupling. The rotation prevention member may comprise an aperture through which the syringe plunger 222 passes, wherein the aperture comprises first keying features configured to correspond to second keying features on the syringe plunger 222 such that the syringe plunger 222 is prevented from rotating. The syringe plunger 222 may be configured such that the second keying features disengage from the first keying features to decouple the syringe plunger 222 from the safety plunger 206. For example, the syringe plunger 222 may be configured to pass through the aperture completely to linearly decouple the syringe plunger 222 from the safety plunger 206.

The contact actuator 110 comprises castellation channels 124a-c. Three castellation channels 124a-c are visible in FIG. 2b, however exemplary auto-injectors may comprise any number of castellation channels 124a-c. The castellation channels 124a-c extend longitudinally (with respect to the auto-injector) from the needle end of the contact actuator 110. The castellation channels 124a-c are different lengths. Each castellation channel 124a-c comprises a mechanical end stop surface at a plunger end of the castellation channel 124a-c. Because the castellation channels 124a-c are of different lengths, each mechanical end stop surface is located at a different distance longitudinally from the needle end of the contact actuator 110.

The castellation channels 124a-c are configured to receive the protrusion 122 of the depth adjustor 108. The depth adjustor 108 is rotatable within the contact actuator 110 to allow the protrusion 122 to align with the desired castellation channel 124a-c. The castellation channels 124a-c may be configured to allow the protrusion 122 to travel within one of the castellation channels 124a-c. The castellation channels 124a-c may be of substantially the same width as the protrusion 122 such that when the protrusion 122 enters one of the castellation channels 124a-c, rotation of the depth adjustor 108 is prevented and only longitudinal movement of the depth adjustor 108 is possible.

The mechanical end stop surfaces are configured to engage with the protrusion 122 of the depth adjustor 108 to set a mechanical limit on the extent of longitudinal movement of the depth adjustor 108 within the contact actuator 110. The contact actuator 110 further comprises arms 130a-b comprising lugs 132a-b configured to engage with the carrier 112 to actuate a plunger driver 134 (e.g. a compression spring).

The carrier 112 is configured to retain the plunger driver 134 in a primed state. The term "primed state" encompasses a plunger driver 134 that is positioned such that it is capable of applying a biasing force. The plunger driver in the exemplary auto-injector 100 is a compression spring 134. In the exemplary auto-injector 100, the compression spring 134 is received within the carrier 112. The compression spring 134 may be fixed to a biasing surface 136 of the carrier 112. In alternative arrangements, the compression spring 134 may abut the biasing surface 136 without being fixed. The other end of the compression spring 134 may be fixed to or abut a surface of the body 114.

The carrier 112 further comprises clips 138a, 138b located on opposed sides of the carrier 112. Each clip comprises a sheath (or syringe) coupling member 140a, 140b and a locking member 141a, 141b joined by a base 142a, 142b. The sheath coupling members 140a, 140b and the locking members 141a, 141b are resiliently deformable. The sheath coupling members 140a, 140b are angled outwardly (with respect to the longitudinal) towards the body of the barrel portion 102. The locking members 141a, 141b are angled inwardly (with respect to the longitudinal of the auto-injector) towards the centre of the barrel portion 102. As such, each clip 138a, 138b is substantially v-shaped.

The compression spring 134 is received within the clips 138a, 138b such that one end of the compression spring 134 abuts the base 142a, 142b of the clips 138a, 138b and the resiliently deformable members 140a, 140b extend either side of the compression spring 134.

The sheath coupling members 140a, 140b comprise a sheath coupling barb 146a, 146b. The locking members 141a, 141b, comprise a locking barb 147a, 147b. The sheath coupling barbs 146a, 146b are configured to engage with a corresponding recess on the sheath of the syringe 200 when the syringe 200 is inserted within the auto-injector 600. The sheath coupling barbs 146a, 146b couple the sheath to the carrier 112 when the sheath coupling barbs 146a, 146b are engaged in the sheath recesses. The locking barbs 147a, 147b are configured to engage with a corresponding recess on the body 114.

Figure 3A:
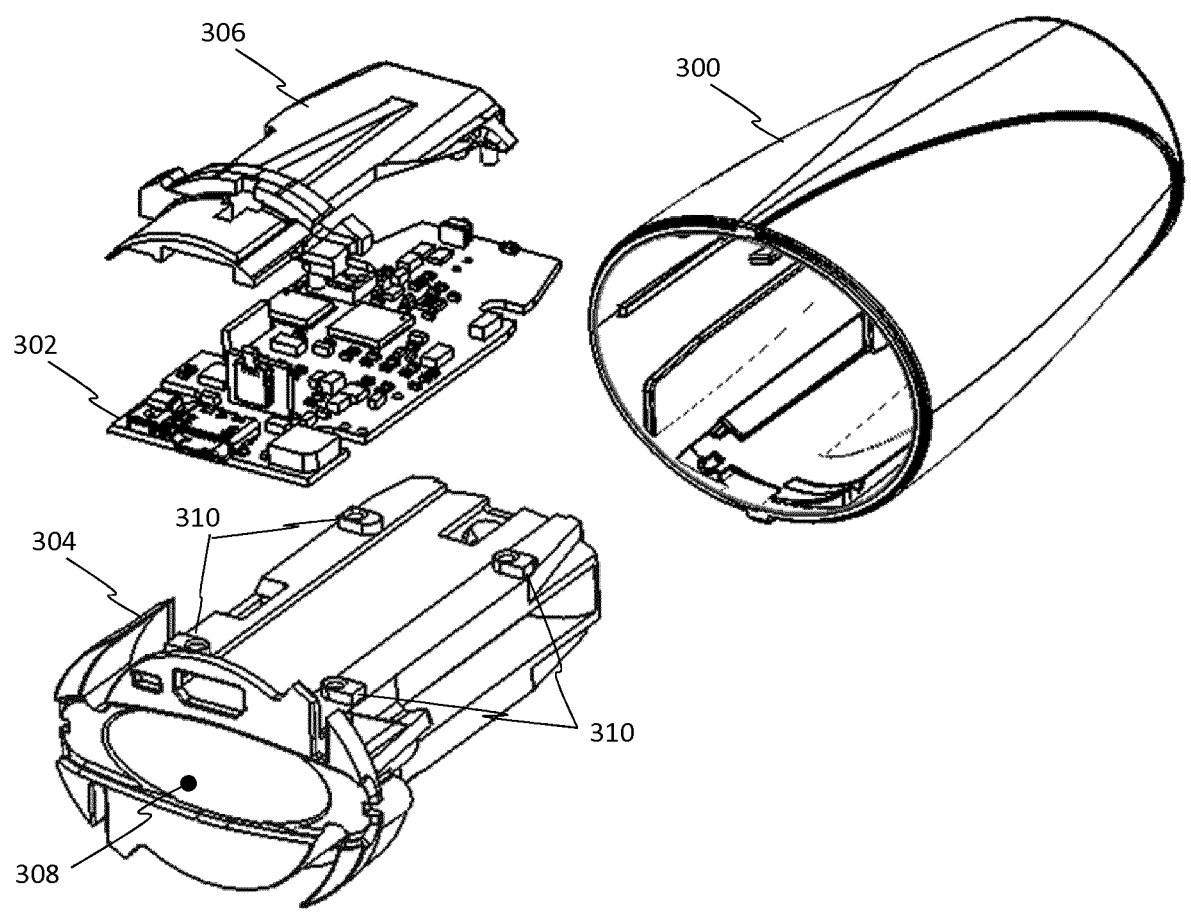
FIG. 3*a* shows an exploded view of a plunger portion of an exemplary auto-injector.

FIG. 3a shows an exploded view of a plunger portion 304 for use with auto-injectors disclosed herein and a plurality of components for fitting within the plunger portion 300. The components comprise: an electrical circuit 302, which in this case is printed on a printed circuit board (PCB) or equivalent; an insert 304 and a circuit cover 306. The electrical circuit may include one or more processors and other electronic components configured to carry out any part of the methods described herein. In particular, the electrical circuit may comprise one or more of: first, second and third detectors; a transmitter; a receiver; and a processor. The insert 304 is configured to be retained within the plunger portion 300 and comprises a channel 308 having an aperture at a needle end for accommodating a safety plunger 206. The safety plunger 206 may travel along the channel 308 towards the plunger end when the syringe is fitted within the auto-injector.

When assembled, the PCB 302 is placed on the insert 304 by positioning locating lugs 310 within corresponding recesses in the PCB 302. The circuit cover 306 is then secured to the insert 304, for example by a snap-fit arrangement, by engaging pins within holes on the locating lugs 310. The assembled features may then be secured in the plunger portion 300.

Figure 3B:
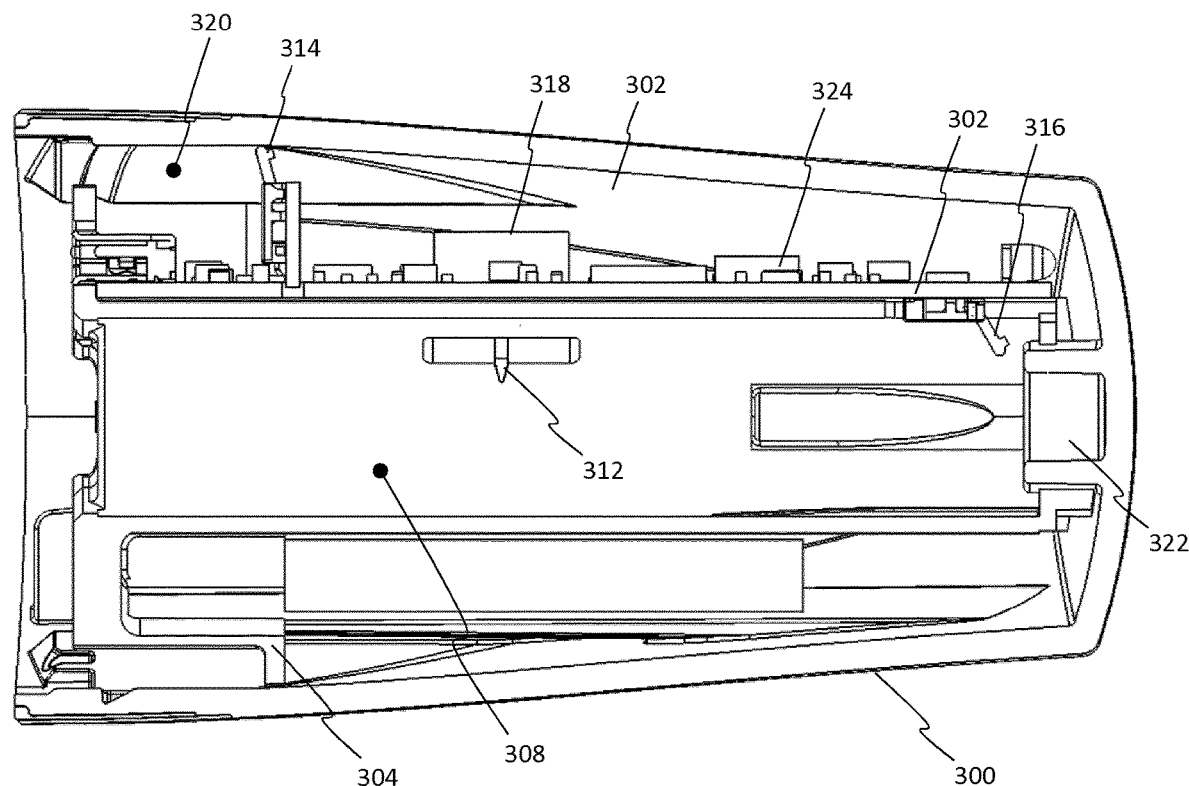
FIG. 3*b* shows a section through a plunger portion of an exemplary auto-injector.

FIG. 3b shows a section through a plunger portion 300 included the assembled circuit 302, insert 304 and circuit cover 306. The PCB 302 comprises a first detector 312, a second detector 314 and a third detector 316. In exemplary arrangements, the first second and third detectors 312, 314, 316 may be micro-switches forming part of the circuit printed on the PCB 302. However, other means for detecting may be used. The PCB 302 may also comprise a plurality of differently coloured light emitting diodes (LEDs), or other visual indicators, and an audio output capable of outputting different audio tones.

In arrangements in which the main body 101 comprises a hinged door, at least part of the PCB may be positioned within the main body 101. Alternatively or in addition, at least part of the PCB may be positioned on the hinged door. In such arrangements, at least part of the PCB may be positioned on an internal surface of the hinged door, such that the PCB is brought into contact with the primed safety syringe when the hinged door is closed. The PCB may be placed on an insert which may be fitted within the main body or on the hinged door.

The first micro-switch 312 may be delivery detector configured to determine whether a full dose delivery has occurred. The term "full dose delivery" encompasses delivery of substantially all of a substance, such as a drug or medicament, from a barrel of a syringe. In particular, the first micro-switch 312 protrudes into the channel 308 such that a part of the safety plunger 206 operates the micro-switch 312, which in turn sends a signal to a processor 318 on the PCB 302. In exemplary arrangements, the micro-switch of the first detector 312 may be configured to be operated in two opposed directions (e.g. towards the needle end and towards the plunger end) and may therefore be configured to detect insertion of the syringe into the plunger portion 300 and to detect full dose delivery. The first micro-switch 312 may be positioned at a point before a point of completion of the delivery stroke. That is, the first switch 312 is positioned to be operable by the safety plunger 206 before completion of the delivery stroke of the syringe plunger 222. Therefore, the first micro-switch 312 may be positioned such that it is operated before full dose delivery. The distance between the position of the first micro-switch 312 and the point of completion of the delivery stroke is to accommodate manufacturing tolerances when manufacturing the syringe.

The second micro-switch 314 may be an assembly detector that is configured to detect when the auto-injector is assembled, that is, when the barrel portion is engaged with the plunger portion 300. The micro-switch of the second detector 314 is positioned in a recess 320 that is configured to receive a protrusion of the body 114 housed within the barrel portion 102. As the barrel portion 102 and the plunger portion 300 are engaged, the protrusion enters the recess 320 and then operates the micro-switch 314. This results in a signal being transmitted to the processor 318. In arrangements in which the main body 101 comprises a hinged door, the second micro-switch may be suitably positioned within the main body or on the hinged door such that the second micro-switch is operated when the hinged door is in a closed position.

The third micro-switch 316 may be a syringe detector that is configured to detect whether a syringe is fitted within the auto-injector. When a syringe is fitted within the auto-injector, the head 204 of the safety plunger 206 travels along the channel 308, optionally actuating the first micro-switch 312 as it passes, and operates the third micro-switch 316 upon engagement of the barrel portion 102 with the plunger portion 300. This results in a signal being transmitted to the processor 318. In arrangements in which the main body 101 comprises a hinged door, the third micro-switch may be suitably positioned within the main body or on the hinged door such that the third micro-switch is operated when the syringe is inserted within the main body.

The plunger portion 300 also comprises a receiver 322 configured to receive a signal emitted from a device of the safety syringe. The signal may include data identifying one or more parameters related to the syringe or a substance contained therein. In exemplary arrangements, the receiver 322 may form part of an RFID reader that is configured to emit an electromagnetic signal that in turn causes an RFID tag on the syringe to emit the signal. The RFID reader 322 may then transmit the data to the processor 318. The transmitter 324 may be configured to use a short range transmission protocol, such as Bluetooth®.

The processor 318 may be configured to control a transmitter 324 to transmit dose data to a user device. The processor 318 may be further configured to time-stamp data.

Operation of the auto-injector is described below.

Prior to use of the auto-injector 100, the barrel portion 102 is separated from the plunger portion 300. As described above, the barrel portion 102 and plunger portion 300 are separated from each other by rotating the plunger portion 300 relative to the barrel portion 102. This separation exposes an opening in the plunger portion 300 through which the syringe 200 may be inserted.

The syringe 200 is pushed into the barrel portion 102 until a click is heard which signifies that the sheath 216 is coupled to the carrier 112. In the exemplary auto-injector 100, insertion of the syringe 200 into the barrel portion 102 deforms the sheath coupling members 147a, 147b to allow the sheath 216 of the syringe 200 to pass through the carrier 112. As the syringe 200 is pushed into the carrier 112, the sheath coupling barbs 146a, 146b travel along the surface of the sheath 216 until they engage with a sheath recess. The engagement of the sheath coupling barbs 146a, 146b with the sheath recesses couples the carrier 112 to the sheath 216 and therefore to the syringe 200.

The plunger portion 300 is then moved over the safety plunger 206 of the syringe 200 such that the safety plunger 206 is received inside the plunger portion 204. The barrel portion 102 and the plunger portion 300 are connected together. The barrel portion 102 and the plunger portion 300 are connected by the user applying a linear force to snap or clip fit the barrel portion 102 and plunger portion 300 together. This may be done by the barrel thread riding over the plunger thread, as discussed above.

As the plunger portion 300 is engaged with the barrel portion 102, the protrusion of the body 114 housed within the barrel portion 102 operates the second micro-switch 314. This results in a signal being transmitted to the processor 318 indicating that the auto-injector is assembled. In addition, the head 204 of the safety plunger 206 operates the first micro-switch 312 in a direction towards the plunger end 100b of the auto-injector. This results in a signal being transmitted to the processor 318 indicating that a syringe is being fitted into the auto-injector. Upon complete assembly of the auto-injector, the third micro-switch is operated by the head 204 of the safety plunger 206. This results in a signal being transmitted to the processor 318 indicating that a syringe 200 is fitted within the auto-injector.

In exemplary arrangements, the processor 318 may determine that a syringe 200 has been correctly fitted within the auto-injector in dependence on the above sequence of events. In exemplary arrangements, all micro-switches must be operated, optionally in a specific order and optionally within specified time limits, for the processor 318 to determine that the syringe 200 has been correctly fitted.

In other exemplary arrangements, fewer micro-switches need to be operated for the processor 318 to determine that a syringe is correctly fitted within the auto-injector. In further arrangements, there is no requirement for the processor 318 to make such a determination at all. For example, in the broadest example, only the first micro-switch 312 is required and it is only required to be operated to determine that full dose has been delivered. In such arrangements, the processor 318 is not required to determine whether the syringe has been correctly fitted and only detects whether full dose delivery has occurred. In other arrangements, actuation of one or more of the micro-switches may be sufficient to determine that the syringe 200 is correctly fitted.

Returning to the exemplary arrangement described in detail herein, the processor 318 has determined that a syringe 200 is correctly fitted within the auto-injector. The RNS remover 106 is then disconnected from the barrel portion 102. The RNS remover 106 is pulled outwards from the barrel portion 102 until an inwardly facing lip is disconnected from the corresponding recess on the barrel portion 102. As the RNS remover 106 is coupled to the RNS 220 fitted to the syringe 200, the RNS 220 is removed from the needle and falls through the RNS remover aperture 116.

In some exemplary arrangements, disconnecting the RNS remover 106 from the barrel portion 102 exposes the depth adjustor 108. Therefore, once the RNS remover 106 has been disconnected from the barrel portion 102, the depth adjustor 108 is at maximum protrusion from the contact actuator 110 (and therefore the barrel portion 102). At this point the lips 120a, 120b of the depth adjustor 108 are engaged with an upper surface of the contact actuator 110. When the depth adjustor 108 is at a maximum protrusion from the contact actuator 110, the depth adjustor 108 is rotatable with respect to the contact actuator 110. The depth adjustor 108 may be rotated in order to align the protrusion 122 of the depth adjustor 108 with the desired castellation channel 124a-d.

In exemplary auto-injectors 100, the depth adjustor 108 may be rotated before removal of the RNS remover 106 using a dial component 149 which may be received by the RNS remover 106. The dial component 149 may be a separate component to the RNS remover 106 configured for insertion thereof or the dial component 149 may be part of the RNS remover 106. In this arrangement, the depth adjustor may comprise teeth located on an internal surface thereof. The depth adjustor teeth may be configured to engage with corresponding teeth located on the dial component 149 when the RNS remover 106 is connected to the barrel. Rotation of the dial component 149 by the user causes a rotation of the depth adjustor 108 due to the engagement of the depth adjustor teeth with the corresponding teeth on the dial component 149.

By allowing the depth adjustor 108 to be rotated, the depth of needle penetration within the injection site before actuation of the compression 134 is able to be set.

Once the protrusion 122 is aligned with the desired castellation channel 124a-d, longitudinal movement of the depth adjustor 108 within the contact actuator 110 causes the protrusion 122 to enter the castellation channel 124a-c with which it is aligned.

Once the protrusion 122 is aligned with the desired castellation channel 124a-c, the depth adjustor 108 may be pressed against the injection site such that the depth adjustor 108 is pushed inside the contact actuator 110. This causes the protrusion 122 to travel within the selected castellation channel 124a-c. Pushing the depth adjustor 108 inside the contact actuator 110, and therefore inside of the barrel portion 102, exposes and pushes the needle of the syringe 200 into the injection site. The depth adjustor 108 continues to move within the contact actuator 110 and the needle continues to be pushed into the injection site until the protrusion 122 engages with the mechanical end stop surface of the castellation channel 124a-c. At this point, the depth adjustor 108 is unable to move within the contact actuator 110 any further and as such, the needle is unable to penetrate into the injection site any further. Selection of a particular castellation channel 124a-c therefore allows the user to customise the depth to which the needle penetrates into an injection site.

After the protrusion 122 meets the mechanical end stop, the contact actuator 110 is linearly coupled to the depth adjustor 108. Therefore, once the protrusion 122 engages with the mechanical end stop surface 126a-d of the castellation channel 124a-c, further longitudinal movement of the depth adjustor 108 within the barrel portion 102 causes longitudinal movement of the contact actuator 110 within the barrel portion 102.

As the contact actuator 110 moves rearwards within the barrel portion 102, the lugs 132a, 132b on the arms 130a, 130b of the contact actuator 110 move along the angled surface of the locking members 140a, 140b. This deforms the locking members 140a, 140 and the locking barbs 146a, 146b are disengaged from the recess on the body 114.

The disengagement of the locking barbs 146a, 146b from the recesses on the body 114 releases the carrier 112 holding the compression spring 134 in the primed state. The compression spring 134 therefore extends. One end of the compression spring 134 is in contact with the biasing surface 136 of the carrier 112. As such, when the compression spring 134 extends, the carrier 112 is pushed towards the bottom of the barrel portion 102.

Because the carrier 112 is connected to the sheath 216 of the syringe 200, the sheath 216 is also pushed towards the needle end 100a of the auto-injector 100. As the sheath 216 is connected to the plunger head 204 by the arms 212a, 212b, the plunger head 204 is driven down. As the syringe plunger 222 is coupled to the safety plunger 206, the syringe plunger 222 is driven into the barrel 214 to inject a substance in the barrel 214 into the injection site.

As the safety plunger 206 and the syringe plunger 222 begin the delivery stroke, the third micro-switch 316 is released. A signal is transmitted to the processor 318 to indicate that the drug delivery process has begun. The processor then enters a delivery sequence and may then control visual and audio indicators to indicate this to a user. For example, the processor 318 may control an LED to flash and may control an audio output to emit a delivery tone. In exemplary arrangements, the processor 318 may be configured to enter the delivery sequence in dependence on a previous determination that the syringe 200 is correctly fitted within the auto-injector.

As the safety plunger 206 and syringe plunger 222 continue on the delivery stroke, the safety plunger 206 operates the first micro-switch 312 towards the needle end at a point at or just before the point of full dose delivery, i.e. the point at which the syringe plunger 222 reaches the end of the barrel 214. In this way, the first micro-switch is able to detect movement of the syringe plunger 222 to a point indicative of full dose delivery. This results in a signal being transmitted to the processor 318 to indicate that full dose delivery has occurred. The first micro-switch 312 may be operable to transmit the signal to the processor 318 in dependence on one or more of the operations/releases of the micro-switches discussed above. For example, the first micro-switch might only be operable if the first, second and/or third micro-switches 312, 314, 316 have previously been operated, and optionally in the order discussed above.

The processor may be configured to remain in the delivery sequence for a period of time after actuation of the first micro-switch 312 to ensure that full dose delivery has occurred. The processor is then configured to control the transmitter 324 to transmit, to a user device, dose data indicating that full dose delivery has occurred.

In some exemplary arrangements, the processor 318 may be configured to enter a fail sequence if a threshold time is exceeded without the first micro-switch 312 being operated. The threshold time may be approximately 10 seconds. In this case, the processor 318 is configured to control the (or a different) LED to emit a different colour and/or flash cycle and may further control the audio output to emit a fail tone, which is different to the delivery tone. In one example, a red LED may be illuminated and may remain illuminated until the auto-injector is disassembled. The processor 318 may be configured to control the transmitter 324 to transmit, to the user device, dose data indicating that the delivery has failed.

The auto-injector 100 may be configured such that the extension of the compression spring 134 to drive the syringe plunger 222 within the barrel 214 continues until the bottom surface 144 of the carrier 112 is in contact with the injection site. Once the carrier 112 is in contact with the injection site, the compression spring 134 is prevented from extending any further. The auto-injector 100 may be configured such that the carrier 112 makes contact with the injection site once the syringe plunger 222 reaches the bottom of the barrel 214 and all of the substance within the barrel 214 has been expelled.

The extension of the compression spring 134 to drive the syringe plunger 222 to the bottom of the barrel 214 takes a period of time, and the user must wait for this. In exemplary auto-injectors 100, the user must wait for approximately 10 seconds.

The user may then move the auto-injector away from the injection site. This allows for continued extension of the compression spring 134. The continued extension of the compression spring 134 moves the carrier 112 and therefore the sheath 216 (which is coupled to the carrier 112) of the syringe 200 over the needle. The extension of the compression spring 134 continues until the sheath 216 fully covers the needle and the carrier 112 partially protrudes from a needle end opening of the barrel portion 102.

After use, the plunger portion 300 of the auto-injector 100 may be removed from the barrel portion 102. The barrel portion 102 is rotated relative to the plunger portion 300 to disengage the barrel thread 103 and the plunger thread 105. The rotation of the plunger portion 300, rotates the syringe 200 within the barrel portion 102. This frees the syringe 200 from the carrier 112 by disengaging the sheath coupling barbs 146b, 146c from the recesses located on the sheath 216 of the syringe 200. This may be done using the cam surface 115 or by deformation of the sheath coupling members 140a, 140b, as discussed above.

Once the sheath coupling barbs 146b, 146c are disengaged from the sheath 216, the syringe 200 and the carrier 112 are decoupled and the syringe 200 may be moved independently of the carrier 112.

The syringe 200 may then be removed from the barrel portion 102. The sheath 216 of the syringe 200 is extended over the needle and this prevents stick injuries.

The compression spring 134 may then be primed again for future use of the auto-injector 100. Once the auto-injector 100 has been moved away from the injection site following use of the auto-injector 100 at the injection site and the syringe 200 has been removed from the auto-injector 200, the compression spring 134 is in an extended state, and the contact actuator 110 and carrier 108 protrude from the barrel portion 102. To prime the compression spring 134, the RNS remover 106 is pushed back into the barrel portion 102.

The RNS remover 106 is pushed into the barrel portion 102. This causes the prongs 118a, 118b of the RNS remover 106 to engage with the bottom surface 144 of the carrier 112 and push the carrier towards the top of the barrel portion 102. The contact actuator 110 is prevented from being pushed back into the barrel portion 110 along with the carrier 112 by the engagement of lock-out protrusions with the opening of the barrel portion 102.

The lock-out protrusions are configured to prevent the contact actuator 110 from being pushed back into the barrel portion 102 until the locking barbs 146a, 146b of the carrier 112 engage with the corresponding recesses on the body 114 of the auto-injector to lock the compression spring 134 into the primed position.

Once the compression spring 134 has been locked into the primed position, further movement of the RNS remover 106 within the barrel portion 102 pushes the lock-out protrusions inwards.

The lock-out protrusions may be pushed inwards by ramps located on an internal surface of the RNS remover 106. The ramps may be located at a distance from the bottom of the RNS remover 106 such that they do not interact with the lock-out protrusions until the RNS remover 106 has been pushed within the barrel portion 102 a distance to engage the locking barbs 146a, 146b with the corresponding recesses on the body 114.

Once the lock-out protrusions have been pushed inwards, further movement of the RNS remover 106 within the barrel portion 102 pushes the contact actuator 110 back into the barrel portion 102 until the RNS remover 106 is reconnected to the barrel portion 102.

In some exemplary arrangements, the processor 318 may be configured to control the RFID reader 322 to interrogate an RFID tag or similar device located on the syringe 200. For example, on determination that the syringe 200 has been correctly fitted within the auto-injector, the processor 318 may instruct the RFID reader 322 to interrogate the RFID tag. The RFID tag may then emit a signal comprising syringe data relating to one or more parameters of the syringe, such as a date that the syringe was filled with a drug, the batch of drug used, the type and identification of the drug etc.

The RFID tag then receives the syringe data and transmits it to the processor 318. The processor is configured to include the syringe data in the dose data to be transmitted to the user device.

In some exemplary arrangements, the processor 318 may be configured to transmit the syringe data to the user device without the dose data. For example, exemplary auto-injectors may include an RFID reader 322 without including the first, second and/or third micro-switches 312, 314, 316. In such cases the syringe data may be transmitted to the user device in isolation.

In exemplary methods and apparatus, the processor 318 is configured to timestamp dose data. This may be done in circumstances when the transmitter 324 is not able to transmit the dose data to the user device. The processor 318 may store the dose data in a memory until such time as a connection to the user device may be established. For example, the processor 318 may wait until the transmitter 324 is able to pair to the user device. The user device is then able to determine the actual time that the dose data was recorded.

Figure 4:
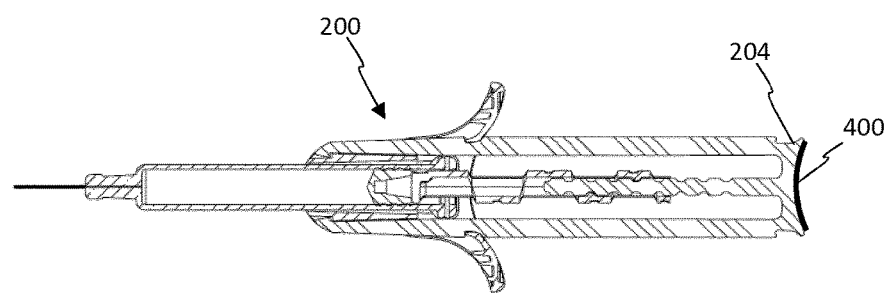
FIG. 4 shows an exemplary syringe.

As shown in FIG. 4, a syringe 200, such as any syringe described herein, may comprise a device 400 configured to emit a signal to the receiver 322 of the auto-injector. The device 400 may in some examples be an RFID tag. The RFID tag may be fitted to the plunger head 204 such that it is positioned in close proximity to the RFID reader 322 when the syringe 200 is fitted within the auto-injector. In other arrangements, the RFID tag 400 may be fitted to another part of the syringe 200 such that it is aligned with and/or within transmission range of the RFID reader 322 when the syringe 200 is fitted within the auto-injector. The RFID tag 400 may be programmed with data relating to one or more parameters of the syringe 200 and/or the contents of the syringe 200, as discussed above.

It is noted that although the above described methods and apparatus include use of a safety syringe, this need not be the case. Exemplary methods and apparatus can be used with a syringe, and in particular arrangements a syringe allowing the plunger driver to be placed below the head of the plunger of the syringe. For example, the methods and apparatus disclosed may comprise a plunger driver configured to couple to the head of the plunger of the syringe from below. This may comprise a direct coupling to the plunger head or an indirect coupling to the plunger head, such as by one or more arms extending from the plunger head towards a needle end of the apparatus.

The skilled person will be able to envisage further embodiments of the invention without departing from the scope of the appended claims.

The invention claimed is:

1. An auto-injector for use with a safety syringe having a syringe plunger, the auto-injector comprising:
   a main body that is openable for receiving the safety syringe and closable before operation of the auto-injector;
   a plunger driver including a spring that is arranged to provide a force to drive the syringe plunger into a barrel of the safety syringe;
   a first detector configured, after activation of the auto-injector, to detect movement of the syringe plunger of the safety syringe to a point on a delivery stroke thereof that is indicative of delivery of a substance from the safety syringe;
   a second detector configured to detect a presence of the safety syringe; and
   a third detector configured to detect that the main body is in a closed position,
      wherein, the first detector is configured to be operable in dependence of the second detector having detected the presence of the safety syringe and the third detector having detected that the main body is in a closed position.

2. The auto-injector according to claim 1, wherein the main body comprises:
   a barrel portion configured to receive the barrel of the safety syringe; and
   a plunger portion configured to receive a plunger of the safety syringe,
      wherein the barrel portion and the plunger portion are configured for detachable engagement, and
      wherein the main body is in the open position when the plunger portion and the barrel portion are detached.

3. The auto-injector according to claim 1, wherein the first detector comprises a micro-switch, operable by a part of the safety syringe during the delivery stroke of the plunger of the safety syringe.

4. The auto-injector according to claim 1, wherein the point on the delivery stroke is reached before completion of the delivery stroke.

5. The auto-injector according to claim 1, comprising one or more indicators configured based on data received from the first detector to indicate whether the full dose was delivered.

6. The auto-injector according to claim 1, further comprising a processor configured to receive signals from the first detector and to control a transmitter to transmit dose data to a user device, the transmitted data indicating whether the full dose was delivered.

7. The auto-injector according to claim 6, wherein the processor is further configured to timestamp the dose data, the auto-injector further comprising a memory for storing the dose data-until a connection to the user device is established by the transmitter.

8. The auto-injector according to claim 1, wherein the second detector comprises a micro-switch.

9. The auto-injector according to claim 8, wherein the main body comprises:
   a barrel portion configured to receive the barrel of the safety syringe; and
   a plunger portion configured to receive a plunger of the safety syringe,
      wherein the barrel portion and the plunger portion are configured for detachable engagement, and wherein the main body is in the open position when the plunger portion and the barrel portion are detached; and
   the switch of the second detector is operable by a feature of the barrel portion during engagement with the plunger portion, or wherein the switch of the second detector is operable by a feature of the plunger portion during engagement with the barrel portion.

10. The auto-injector according to claim 9, wherein the second detector is positioned in the plunger portion.

11. The auto-injector according to claim 1, further comprising a receiver configured to receive a signal emitted from a device of the safety syringe and comprising syringe data identifying one or more parameters related to the safety syringe.

12. The auto-injector according to claim 11, wherein the receiver forms part of a Radio Frequency Identification, RFID, device configured to transmit a Radio Frequency, RF, signal to cause the device of the safety syringe to emit the received signal.

13. The auto-injector according to claim 1, further comprising a processor configured to receive signals from the first detector and to control a transmitter to transmit dose data to a user device, the transmitted data indicating whether the full dose was delivered, wherein the processor is configured to include the syringe data in the dose data for transmission by the transmitter.

14. The auto-injector according to claim 1, wherein the plunger driver is for coupling to a plunger head of the syringe when the syringe is fitted within the auto-injector, and wherein the plunger driver is positioned on the auto-injector such that it is below the plunger head when the syringe is and fitted within the auto-injector.

15. The auto-injector according to claim 14, wherein the plunger driver is positioned such that it is below the plunger head after use of the syringe.

16. The auto-injector according to claim 14, wherein the plunger driver is configured to couple to at least one arm coupled to the plunger head and extending towards a needle end of the auto-injector when the syringe is fitted thereto.

17. The auto-injector according to claim 1, wherein the spring is a compression spring.

18. The auto-injector according to claim 1, further comprising a safety syringe.

19. The auto-injector according to claim 17, wherein the plunger driver is for coupling to a plunger head of the syringe when the syringe is fitted within the auto-injector, and wherein the plunger driver is positioned on the auto-injector such that it is below the plunger head when the syringe is and fitted within the auto-injector and wherein the syringe comprises:

a plunger having a head; and at least one arm extending longitudinally from the head of the plunger towards a needle end of the safety syringe and configured to engage with the plunger driver, such that extension of the plunger driver drives the plunger into the barrel of the safety syringe.

* * * * *